US007112177B2

(12) United States Patent
Christensen et al.

(10) Patent No.: US 7,112,177 B2
(45) Date of Patent: Sep. 26, 2006

(54) APPARATUS FOR MONITORING INTRA-ABDOMINAL PRESSURE

(75) Inventors: Mark A. Christensen, Salt Lake City, UT (US); Timothy R. Wolfe, Salt Lake City, UT (US); Perry W. Croll, Salt Lake City, UT (US); Marshall T. Denton, Salt Lake City, UT (US); Edward J. Kimball, Salt Lake City, UT (US)

(73) Assignee: Wolfe Tory Medical, Inc., Salt Lake City, UT (US)

( * ) Notice: Subject to any disclaimer, the term of this patent is extended or adjusted under 35 U.S.C. 154(b) by 454 days.

(21) Appl. No.: 10/379,222

(22) Filed: Mar. 4, 2003

(65) Prior Publication Data

US 2004/0176703 A1    Sep. 9, 2004

(51) Int. Cl.
*A61B 5/00* (2006.01)
(52) U.S. Cl. ..................................... 600/561
(58) Field of Classification Search ............... 600/561, 600/573, 587; 604/317, 328; 137/625, 527, 137/602, 624.45, 625.4, 595, 605, 876, 630.16, 137/843, 532, 533; D23/244; 73/265; 251/326, 251/304, 329
See application file for complete search history.

(56) References Cited

U.S. PATENT DOCUMENTS

| 1,666,332 | A | * | 4/1928 | Hirsch | ......................... 73/747 |
| 1,712,848 | A | * | 5/1929 | Rose | ......................... 600/561 |
| 3,620,255 | A | * | 11/1971 | Stillman | ................. 137/625.45 |
| 3,794,043 | A | * | 2/1974 | McGinnis | .............. 128/207.15 |
| 4,210,173 | A | * | 7/1980 | Choksi et al. | ........... 137/512.3 |
| 4,217,911 | A |   | 8/1980 | Layton | |
| 4,301,811 | A | * | 11/1981 | Layton | ......................... 600/561 |
| 4,966,161 | A | * | 10/1990 | Wallace et al. | ............. 600/561 |
| 5,385,563 | A |   | 1/1995 | Gross | |
| 5,713,850 | A | * | 2/1998 | Heilmann et al. | ............ 604/28 |
| 5,865,764 | A | * | 2/1999 | Moorhead | ................... 600/561 |

(Continued)

FOREIGN PATENT DOCUMENTS

EP          0 258 690         8/1987

(Continued)

OTHER PUBLICATIONS

Fusco, Mark A., et al. "Estimation of Intra-abdominal Pressure by Bladder Pressure Measurement: Validity and Methodology," 50(2) The Journal og TRAUMA® Injury, Infection, and Criitical Care 297-302 (Feb. 2001).

(Continued)

*Primary Examiner*—Max F. Hindenburg
*Assistant Examiner*—Matthew Dryden
(74) *Attorney, Agent, or Firm*—TraskBritt

(57) ABSTRACT

An apparatus for monitoring intra-abdominal pressure in a medical patient includes a urinary catheter connected to a urine valve having selectable communication positions between a discharge end of the urinary catheter and either a drain or a fluid source. Preferably, the urine valve has a housing adapted to resist patient discomfort from body-valve contact. A plumbing structure desirably maintains fluid supply and drain conduits in a substantially parallel arrangement to assist routing those conduits between a patient's legs. When the urine valve is oriented for communication with the fluid source, a syringe may be used to introduce a known quantity of fluid through the urine valve into the patient's bladder where the fluid's pressure can be measured. Desirably, a double check valve is included in a fluid supply path and arranged to permit repetitive operation of the syringe to introduce a bolus of fluid into the patient's bladder.

26 Claims, 10 Drawing Sheets

U.S. PATENT DOCUMENTS

| | | | |
|---|---|---|---|
| 6,494,208 B1 * | 12/2002 | Morejon | 128/207.15 |
| 6,503,208 B1 * | 1/2003 | Skovlund | 600/561 |
| 2002/0065472 A1 | 5/2002 | Brockway et al. | |

FOREIGN PATENT DOCUMENTS

WO     WO 2004/080519 A1     9/2004

OTHER PUBLICATIONS

Kirkpatrick, Andrew W., et al., "Is Clinical Examination an Accurate Indicator of Raised Intra-abdominal Pressure in Critically Injured Patients?" 43(3) CJS 207-211 (Jun. 2000).

Lozen, Yvonne "Intraabdominal Hypertension and Abdominal Compartment Syndrome in Trauma: Pathophysiology and Interventions," 10(1) AACN Clinical Issues: Advanced Practice in Acute Critical Care 104-112 (Feb. 1999), http://gateway2.ovid.com/ovidweb.cgi (11 pages) Dec. 9, 2002.

Malbrain, M.L.N.G., "Abdominal pressure in the critically ill: measurement and clinical relevance," 25 Invensive Care Med. 1453-1458 (1999).

Surgue, Michael, "Intra-abdominal presure: time for clinical practice guidelines?" 28 Intensive Care Med. 389-391 (2002).

PCT Internationl Search Report, PCT/AU2004/000282, dated Apr. 28, 2004.

PCT Writtern Opinion, PCT/AU2004/000282, dated Apr. 28, 2004.

* cited by examiner

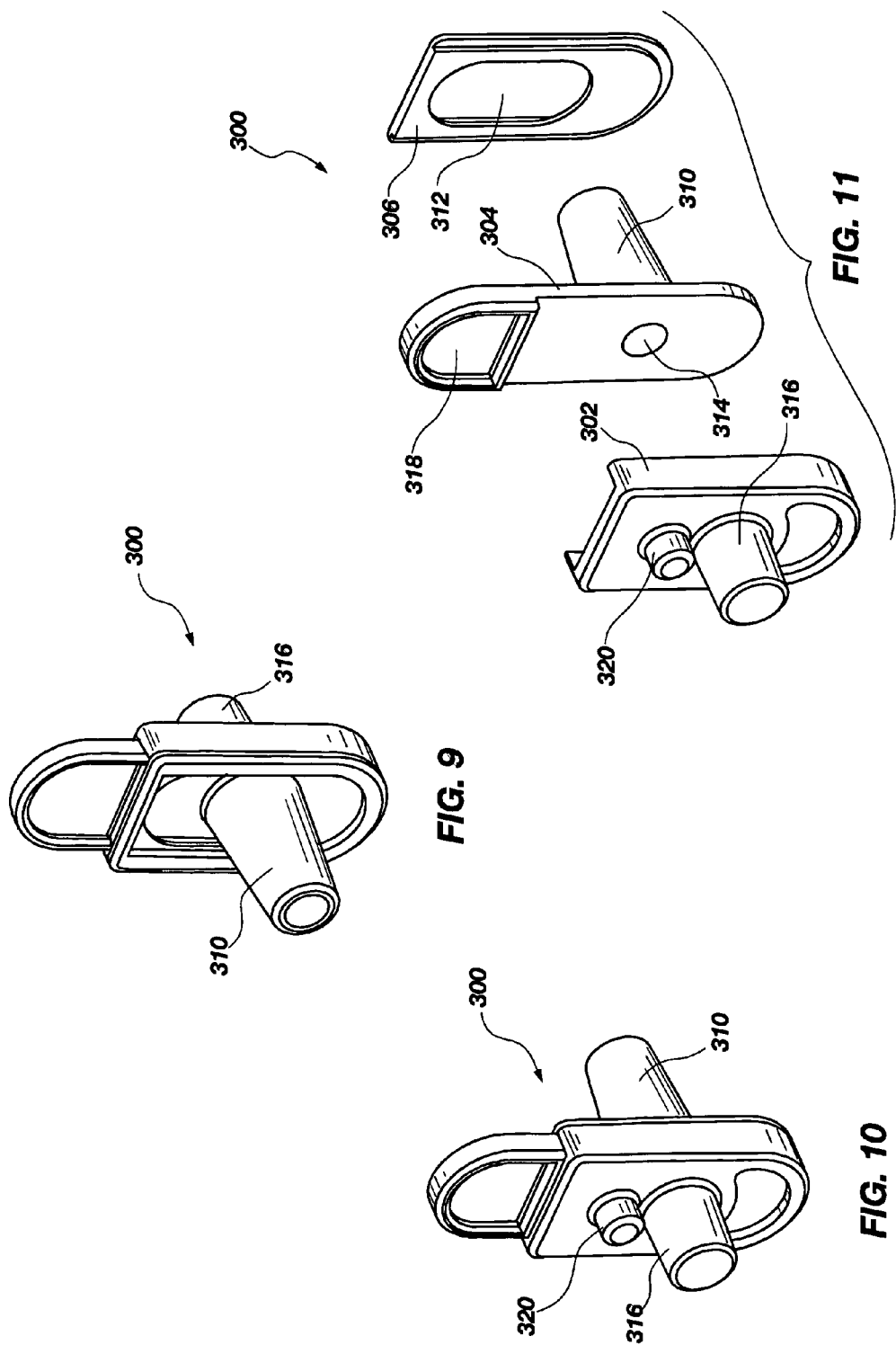

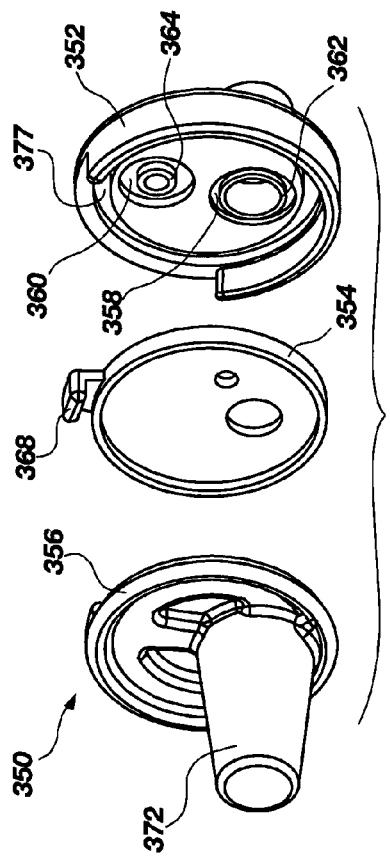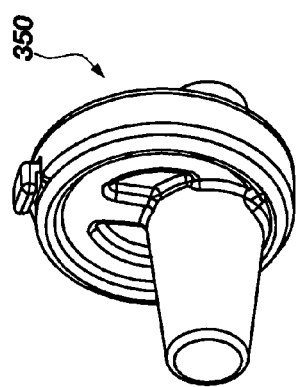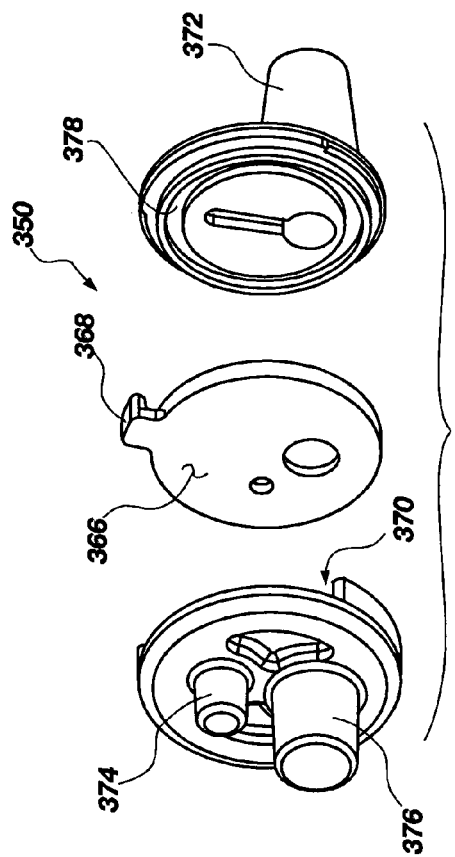

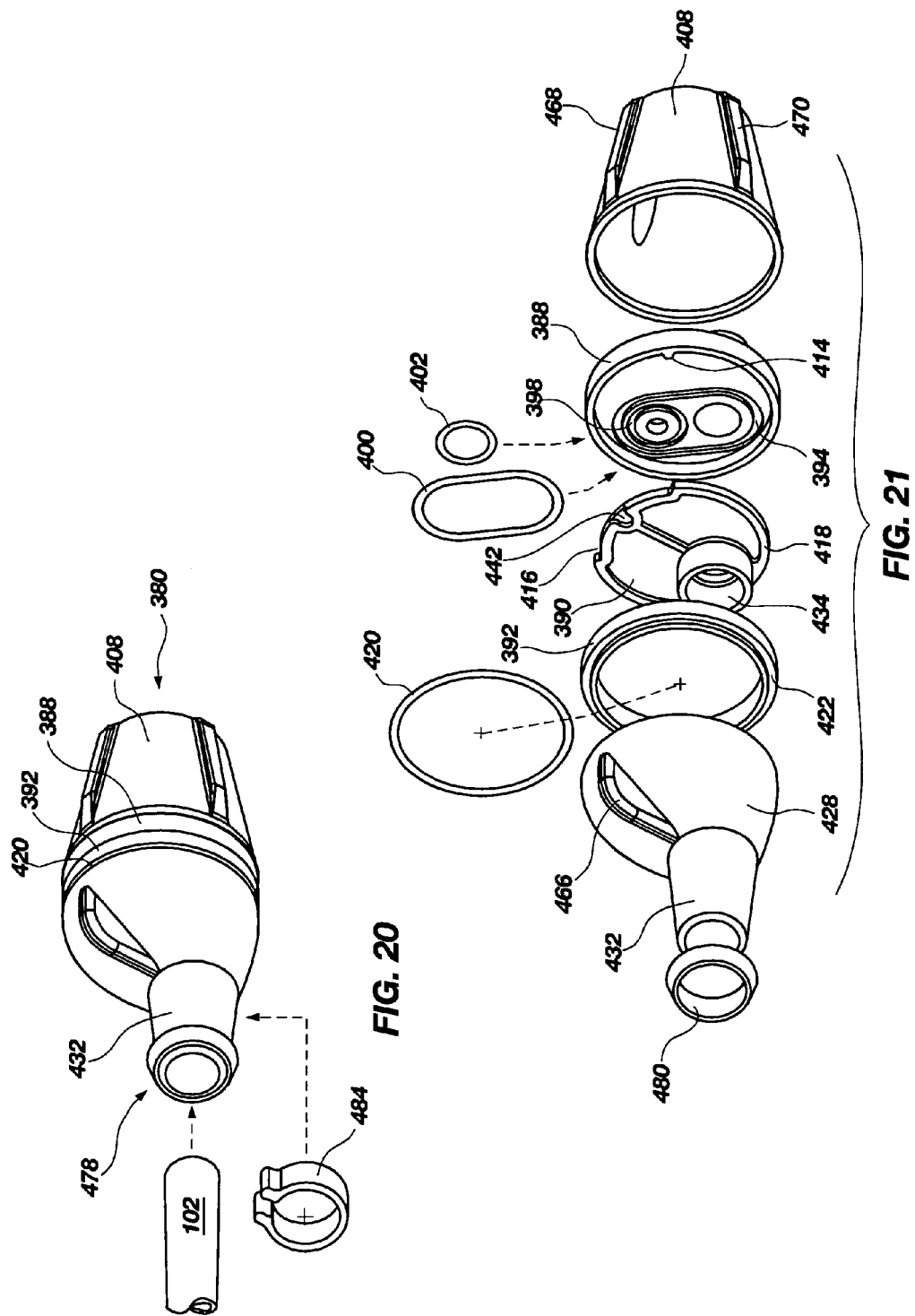

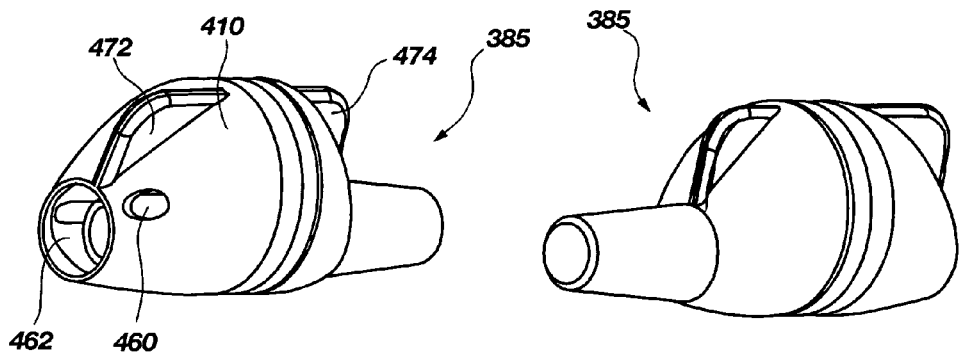
FIG. 26  FIG. 24
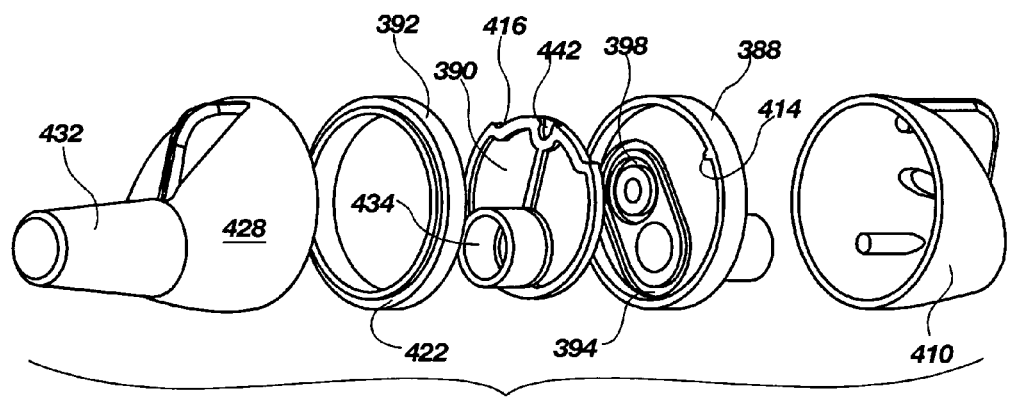
FIG. 25
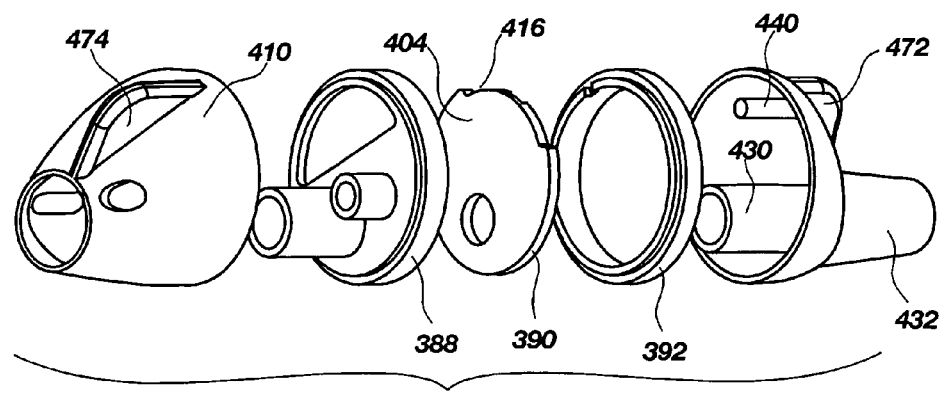
FIG. 27

APPARATUS FOR MONITORING INTRA-ABDOMINAL PRESSURE

BACKGROUND OF THE INVENTION

1. Field of the Invention

The invention relates generally to plumbing devices, including valves and conduits, and to pressure measurement equipment. The invention relates particularly to apparatus configured as an assembly to monitor intra-abdominal pressure of a medical patient.

2. State of the Art

It has been determined that the intra-abdominal pressure of a medical patient can be used as a diagnostic tool to assess progress of the patient's recovery subsequent to a medical procedure. For example, the intra-abdominal pressure of the patient can be expected to increase subsequent to a surgical procedure due to fluid leakage and edema in the abdominal cavity. By monitoring the patient's intra-abdominal pressure, a practitioner may receive advance warning of complications resulting from the surgical procedure. In such case, the practitioner may be better prepared to take adequate counter-measures before the patient displays perceptible outward signs of distress and before a life-threatening situation may develop.

Currently employed techniques used to monitor a patient's intra-abdominal pressure are adapted to measure the pressure of fluid contained within the patient's bladder at intervals spaced apart in time. While the pressure reading at a pressure transducer may not correspond to the actual value of intra-abdominal pressure, trends in measured pressure will correlate to trends in intra abdominal intra-abdominal pressure in the patient.

One way to measure a patient's intra-abdominal pressure involves disassembling a urinary catheter drain tube to inject saline through the catheter and into the patient's bladder. (For convenience, a urinary catheter will generally be referred to in this disclosure as a Foley catheter, due to its common use). Unfortunately, opening the closed drainage system plumbing places both the patient and the health care practitioner at increased risk of infection. It is possible to use a three-way Foley catheter, but such catheters are more expensive and are not routinely used. Use of a three-way Foley catheter would require either pre-knowledge of its necessity or replacement of a standard catheter. The former option increases costs and the latter would increase both costs and risk of patient infection.

A different approach for introducing a bolus of fluid into a patient's bladder incorporates the aspiration port included in a urinary catheter drain system as a fluid injection port. The drain tube connected to the Foley catheter is blocked, and the needle of a syringe is passed through the catheter's aspiration port to permit injection of a saline bolus. After the injection needle is removed, a needle for a manometer or pressure transducer is then inserted through the aspiration port to record bladder pressure. Undesirably, approaches involving use of needles, particularly in the vicinity of the patient's legs, to assemble the pressure measuring apparatus place both the patient and the health care practitioner at risk of needle sticks.

With reference to FIG. 1, a currently preferred arrangement adapted to monitor a medical patient's intra-abdominal pressure is generally indicated at 100. A patient is fitted with a urinary catheter 102, such as a Foley catheter. A fluid source, such as saline bag 104, is connected in fluid communication to the catheter 102 upstream of an occluding device 108 temporarily applied to block the catheter drain conduit 106. Interruption of the urine drain path from the patient generally is permitted only temporarily as required to effect pressure measurements.

The device 100 includes a pair of two-way or three-way stopcocks, 110 and 112, respectively. One end of fluid supply tube 114 is connected to a one liter saline bag 104. The other end of fluid supply tube 114 is connected to an inlet port of stopcock 110. A valve stem in stopcock 10 may be oriented to permit fluid to flow from bag 104 toward syringe 116. When syringe 16 is full, or charged with fluid as desired, the valve stem of stopcock 110 is adjusted by way of a manual rotation to permit fluid flow from the syringe toward stopcock 112 while resisting fluid flow toward bag 104. Stopcock 112 can be adjusted to direct a bolus of fluid from syringe 116 for flow through tubing 120 towards catheter 102. Stopcock 112 may also be adjusted to an alternate configuration to provide fluid communication between a pressure measuring device 121 and tubing 120 while resisting fluid flow toward stopcock 110. An infusion needle or angiocatheter 122 carried at an end of tubing 120 is inserted into urine collection port 125 to couple the tube 120 in fluid communication with the catheter 102.

The steps typically required to measure a patient's intra-abdominal pressure, using the arrangement of FIG. 1, are as follows: First the apparatus 100 is assembled, including inserting the needle of an angiocatheter 122 into aspiration port 125 connected to a Foley catheter 102 installed in a patient. Stopcock 110 is oriented to permit fluid flow between bag 104 and syringe 116, and the syringe is filled with saline. Stopcocks 110 and 112 are then both adjusted for fluid flow from the syringe 116 toward the catheter 102. Tube 120 is flushed and filled with saline. Then tubing 106 is occluded to resist fluid flow in a drain direction from catheter 102. Typically, stopcock 112 is then adjusted to resist fluid flow toward syringe 116 and stopcock 110 is configured to permit fluid flow between bag 104 and syringe 116 so that the syringe 116 can be refilled with saline. After priming syringe 116, stopcocks 110 and 112 are adjusted for fluid flow between syringe 116 and catheter 102, whereby to introduce a bolus of fluid into the patient's bladder. Then, stopcock 112 is oriented to provide fluid communication between conduit 120 and pressure transducer 121 while resisting fluid flow toward stopcock 110. Pressure apparatus 121 then indicates the current pressure in the patient's bladder, which may be correlated to intra-abdominal pressure. Subsequent to making and recording the pressure measurement, the occlusion of drain 106 is removed to permit draining the bolus of fluid from the patient's bladder. Such procedure is repeated at intervals spaced apart in time to record trends in the patient's intra-abdominal pressure. The bolus of injected fluid desirably is less than about 100 mL and of uniform size during each successive pressure measurement to avoid effect from bladder wall musculature.

Occluding device 108 may be a clamp or hemostat as illustrated, or sometimes may be a valve. However, operable medical grade valves that are commercially available, such as two-way or three-way stopcocks 110 and 112, typically introduce undesired complications. One complication is that the available medical grade stopcocks typically provide drainage passageways that are too small in diameter for use in a urinary catheter drain. Clogging of the drain bore would be a serious problem.

The location of a catheter drain-occluding valve for a pressure measurement system desirably is in close proximity to the catheter 102—therefore between the patient's legs. Another complication substantially precluding direct inclusion of available medical grade two-way or three-way valves or stopcocks is that such devices route fluid conduits in orthogonal directions at the valve connection locations, thereby creating protruding and invasive plumbing that is uncomfortable to the patient. Furthermore, currently available valves and stopcocks also have protrusions (such as valve actuators or handles), and sharp corners or abrupt changes in shape, that place a patient at risk of injury should such protrusion or corner be impressed into a patient's skin.

The procedures for measuring trends in a patient's intra-abdominal pressure described above undesirably place a patient at risk of infection, or require tiresome manual adjustment of a plurality of plumbing devices, such as two-way valves or stopcocks. It would be a desirable improvement over the prior art to provide a device for measuring trends in a patient's intra-abdominal pressure that is faster and more simple to operate. It would be a further advance over the prior art to eliminate operations requiring needles to assemble or use the pressure measurement apparatus. A still further advance in the art would be to enhance the patient's comfort and increase the patient's protection from injury by minimizing or avoiding contact between the patient and uncomfortable or even harmful medical apparatus.

BRIEF SUMMARY OF THE INVENTION

An apparatus and method for measuring hydraulic pressure in the bladder of a medical patient whereby to infer intra-abdominal pressure (IAP). The apparatus may be embodied to include a catheter adapted for draining urine from a patient, a container of fluid, a fluid pump disposed to urge fluid flow from the container toward the patient's bladder, a pressure transducer configured to measure a pressure of fluid in the bladder, and an automatic flow-control device. The automatic flow control device is actuated, at least in part, by fluid pressure generated by the pump. Preferred flow-control devices are operable to permit flow of fluid from the container toward the pump and to resist flow of fluid from the pump back toward the container. The flow-control device desirably also permits flow of fluid in a direction from the pump toward the catheter and resists flow of the fluid in a direction from the pressure transducer toward the pump. A flow-control device may be embodied as a double check valve or as a check-bypass valve functional as a double check valve. Operable pumps include a syringe disposed to effect a cyclic fluid pressure at a staging area between first and second operable check valve portions of the double check valve. Commonly, the check valve is attached to a discharge end of the syringe. The combination of the double check valve and a syringe enhances the speed at which intra-abdominal pressure measurement can be performed.

A urine valve desirably is included in the IAP apparatus to further facilitate making a pressure measurement. The urine valve is typically arranged to provide a first flow portion disposed in a first fluid path from the container of fluid, a second flow portion disposed in a second fluid path operable as a drain for fluid received from the catheter and discharged through the urine valve, and a third flow portion disposed for fluid communication with a urine discharge end of the catheter. To speed up the IAP measurement, a urine valve is operable selectively to resist fluid flow between the third flow portion and the second flow portion. A urine valve is further operable selectively to resist fluid flow between the first flow portion and the third flow portion.

A urine valve may be shaped to assist in routing of fluid conduits in the space between a patient's legs. Desirably, the first and second flow portions of the urine valve provide structure configured to permit connection to respective first and second substantially parallel conduits whereby to facilitate routing those conduits between a patient's legs. It is further desirable for first, second, and third flow portions of the urine valve to include substantially parallel conduit sections to streamline the fluid conduit plumbing arrangement. Sometimes, alternative connection structure is provided in fluid communication with each of the first, second, and third flow portions of the urine valve for connection to first, second, and third substantially parallel conduits, whereby to facilitate routing those substantially parallel conduits in a space between a patient's legs. Connection structure within contemplation includes angle fittings.

Urine valves may be actuated in many ways to select a flow path through the valve. In a preferred embodiment, a flow path through the urine valve is selected by rotating a first valve structure with respect to a second valve structure. The operable fluid flow path can be selected by rotating a first portion of a valve housing with respect to a second portion of the housing. In the latter arrangement, first and second portions of the housing are typically sealed against infiltration by external contaminants. Desirably, structure carried on the housing of the urine valve is adapted to provide visual indication of a currently selected flow path.

One currently preferred urine valve includes first and second apertures, opening to portions of respective first and second flow paths through the valve, that are disposed on a first surface. A valve core element includes a second surface structured in cooperation with the first surface such that a third aperture disposed on the second surface can be aligned to form a leak resistant seal for fluid communication with either of the first and second apertures. The third aperture opens to a portion of a flow path in common to the first and second flow paths. The first and second surfaces can be flat, planar, or may be curved in various directions. In a preferred embodiment of a urine valve, the leak resistant seal includes first and second O-rings. The first O-ring is disposed on the first surface and arranged to encompass the first aperture. The second O-ring is disposed on the first surface and arranged to encompass the first aperture and the second aperture.

Commonly, a body of the urine valve includes a housing structured to resist imparting contact injury to a patient. It is further desirable for a protective housing to include smooth surfaces and rounded corners to resist formation of crevices in which contaminants might be shielded, whereby to facilitate cleaning fecal matter, or other patient excretions, from an exterior surface of the housing.

A protective tray may be provided as an alternative to, or in addition to, a protective valve housing. Such a tray is operable as a protective housing and generally includes blunt corners and areas of gradual transition in curvature whereby to resist injury to a patient arising from contact with the tray. The tray typically defines a socket operable to space structure received in the socket apart from a patient. For example, a socket may be structured to receive a urine valve. The socket may further accommodate a discharge end portion of structure associated with the catheter. Certain sockets are adapted to hold the discharge end portion of a catheter in a preferred orientation whereby to assist a health care practitioner in inserting a needle into the catheter's aspiration port.

An alternative embodiment of an IAP apparatus may include a catheter adapted for draining urine from the patient, a container of fluid, a fluid pump, a pressure transducer arranged to measure a pressure of the fluid at a location downstream of the pump, and a multi-way urine valve. The multi-way urine valve includes first, second and third flow portions. The first flow portion of the valve is disposed in a first fluid path arranged to transfer fluid from the container to the catheter. The second flow portion is disposed in a second fluid path configured as a drain for the catheter. The third flow portion is disposed in the first fluid path for fluid communication between the valve and a discharge end of the catheter. In use, the multi-way valve is operable selectively to resist fluid flow between at least the third flow portion and the second flow portion. Desirably, a urine draining lumen forming a flow path through the valve has a diameter in excess of about 3/16 inches to resist occlusion from a build-up of matter discharged from the patient's bladder. Furthermore, a sealing element of the multi-way valve is desirably structured to contain a dead volume of less than about 0.001 cubic inch to reduce contaminant containment, whereby to resist infection transmission.

A method for measuring hydrostatic pressure in the bladder of a medical patient typically includes the steps of: a) installing a urinary catheter to provide fluid communication on a first fluid path between the bladder and a discharge portion of the catheter; b) affixing a urine valve (having drain and measure orientations) to the catheter; c) connecting a source of fluid to a pump operable to urge the fluid toward the catheter; d) disposing a pressure transducer between the pump and bladder to measure the fluid's pressure; e) placing the urine valve into the measure orientation and operating the pump to introduce a bolus of the fluid into the bladder; f) using the pressure transducer to measure a hydrostatic pressure of the fluid; and g) placing the urine valve into the drain orientation to empty the bladder. Usually, steps e) through g) are repeated in sequence as an intra-abdominal pressure measurement procedure is performed a plurality of instances that are spaced apart in time. Desirably, operation of the pump in step e) entails actuation of a syringe to cause cyclic pressure fluctuation at a staging area of an automatic valve arrangement operable to permit fluid flow from the fluid source toward the catheter and to resist fluid flow in a reverse direction.

BRIEF DESCRIPTION OF THE DRAWINGS

In the drawings, which illustrate what are currently considered to be the best mode/modes for carrying out the invention:

FIG. 9 is a view in perspective from a proximal end of a first urine valve;

FIG. 10 is a view in perspective from a distal end of the urine valve illustrated in FIG. 9;

FIG. 11 is an exploded view in perspective of the urine valve illustrated in FIG. 10;

FIG. 16 is a view in perspective from a proximal end of a third urine valve;

FIG. 17 is an exploded view in perspective of the urine valve illustrated in FIG. 16;

FIG. 18 is a view in perspective from a distal end of the third urine valve;

FIG. 19 is an exploded view in perspective of the urine valve illustrated in FIG. 18;

FIG. 20 is a view in perspective from a proximal end of a fourth urine valve;

FIG. 21 is an exploded view in perspective of the urine valve illustrated in FIG. 20;

FIG. 24 is a view in perspective from a proximal end of a fifth urine valve;

FIG. 25 is an exploded view in perspective of the urine valve illustrated in FIG. 24;

FIG. 26 is a view in perspective from a distal end of the fifth urine valve; and FIG. 27 is an exploded view in perspective of the urine valve illustrated in FIG. 26.

DETAILED DESCRIPTION OF THE ILLUSTRATED EMBODIMENTS

Figure 2:
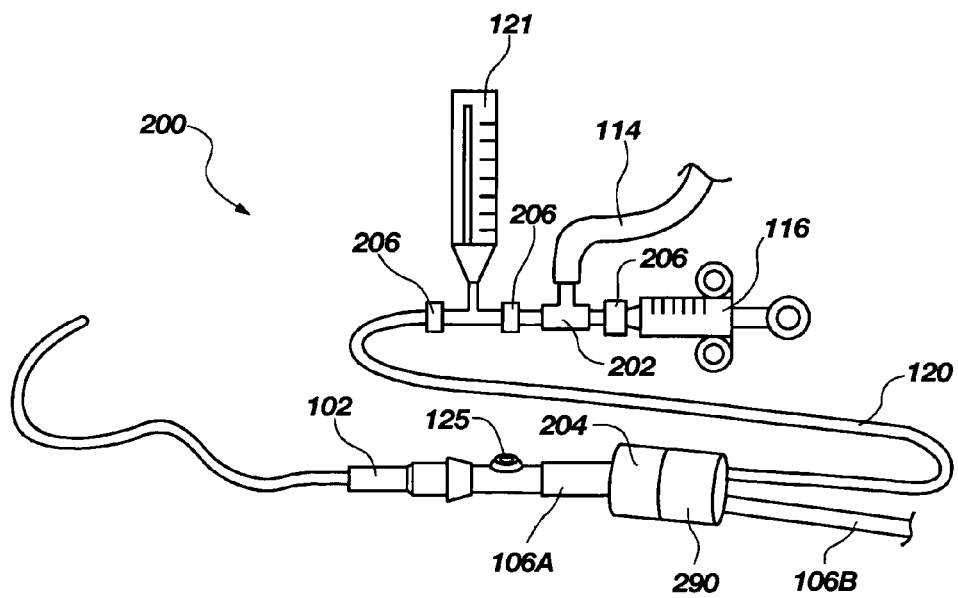
FIG. 2 illustrates a first currently preferred assembly for measuring a patient's bladder pressure.

FIG. 2 illustrates a currently preferred embodiment, generally indicated at 200, of an apparatus for measuring trends in a patient's intra-abdominal pressure. The assembly 200 includes a conduit 114 with one end in fluid communication with a saline or other fluid source (not illustrated). Conduit 114 desirably is connected at a second end for fluid communication with an automatic direction-of-flow control device 202. Flow control device 202 can generally be characterized as being cyclically operable with a staging pump, such as syringe 116, to permit fluid flow from a fluid source during a filling stroke of the staging pump and to resist fluid flow towards the fluid source during an expelling stroke of the staging pump. Typically, one or more seal members carried inside of device 202 is/are biased for automatic operation to control a direction of fluid flow through the device 202. Therefore, a health care practitioner is relieved of the tedious chore of adjusting the valve 202 manually to control a direction of fluid flow. Devices within contemplation for use as a flow control device 202 include a pair or more of check valves, double check valves, and check-bypass valves. Inclusion of an automatically actuated flow-control device 202 constitutes a first improvement over prior art assemblies.

As illustrated in FIG. 2, assembly 200 may optionally include a two-way valve 204 connected in fluid communication with a discharge port from flow control device 202. Two-way valve 204 may sometimes also be referred to in this disclosure as a urine valve or a urine discharge valve. For purposes of the invention, a two-way valve places a first conduit into selective fluid communication with either one or the other of two additional conduits. A three-way valve would also be operable, but there is not much need for a fluid supply port to communicate directly with a drain port in application of the instant invention. Valve 204 desirably is located in close proximity to a discharge of a Foley catheter 102 installed in a patient. A Foley catheter is not required, per se. Virtually any sort of urine draining catheter may be used.

As illustrated in FIG. 2, valve 204 is connected in fluid communication with Foley catheter 102 by way of a relatively short section of urine drain conduit 106A. Such close proximity to a discharge of catheter 102 reduces the volume of fluid required to be pumped through the system to effect a pressure measurement and also helps to maintain the apparatus 200 in a tidy, organized arrangement. Inclusion of a two-way valve, such as valve 204, to selectively block a discharge from the catheter 102 simplifies operation of the assembly 200 compared to the prior art and constitutes a second improvement over the prior art, providing several advantages.

Figure 1:
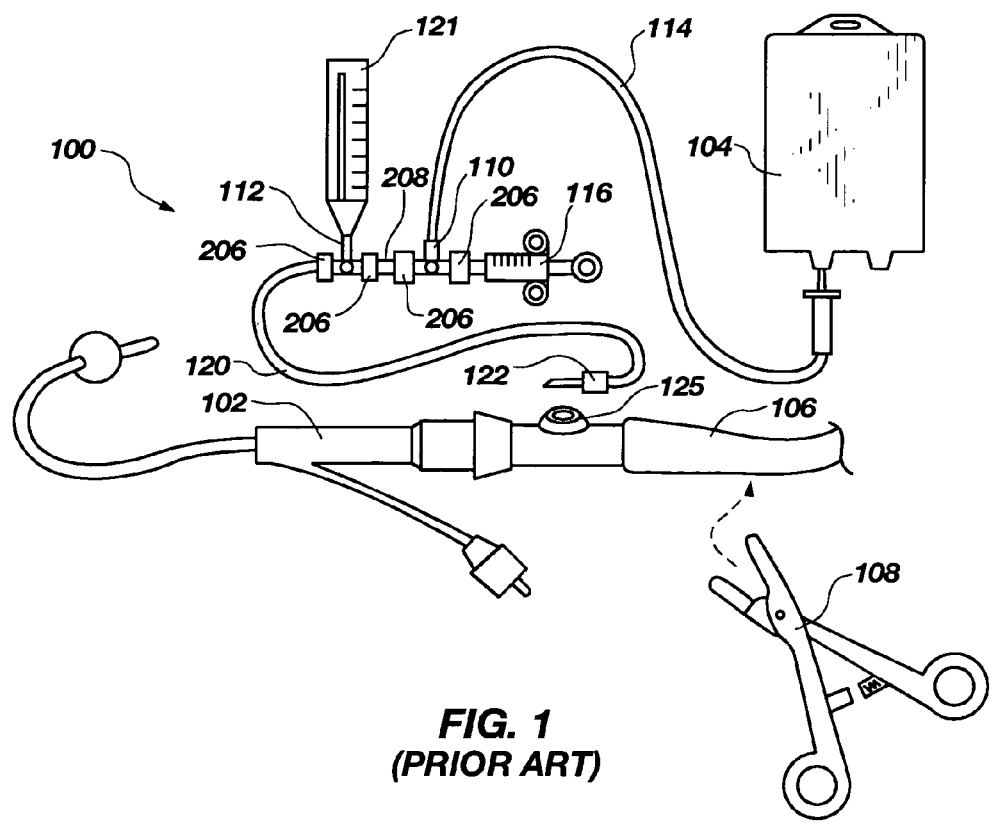
FIG. 1 illustrates a prior art assembly operable to measure a patient's bladder pressure.

Of course, a valve 204 may be adapted to connect directly to the discharge end of a urinary catheter without an intervening conduit section 106A. It is within contemplation for a valve 204 to carry structure(s) adapted for connection directly to structure(s) provided at a discharge area of a catheter. In general, connections between the various components forming an assembly 200 may be made as a matter of convenience and using any operable type of plumbing connection joint. In the embodiment illustrated in FIG. 2, valve 202 may be connected to a discharge end of syringe 116 through a luer-locking type of joint 206. An alternative connection between any of the components in an intra-abdominal pressure measuring assembly according to the invention, such as assembly 200, may include any operable fluid-tight connection formable between the components. Stretches between components may also include intermediate structure(s), such as one or more sections of tubing 208 (see FIG. 1). Furthermore, the assembly 200 desirably is configured for arrangement of its various components in convenient locations. For example, bag 104 typically is suspended from an elevated hanger, but pressure indicating manometer 121, or more specifically, its transducer portion, desirably is located at approximately the same elevation as the patient's bladder to reflect an equivalent pressure.

With continued reference to FIG. 2, preferred embodiments of a two-way valve 204 provide connections for fluid supply conduit 120 and urine drain conduit 106B to place such conduits approximately in parallel. A substantially parallel arrangement of conduits 120 and 106B near the valve 204 increases patient comfort and also helps to maintain a tidy arrangement of assembly 200. Furthermore, the substantially in-line arrangement between conduit 106A and conduits 120 and 106B illustrated in FIG. 2 aides in routing the conduits in a path to minimize their intrusiveness to a patient.

Figure 3:
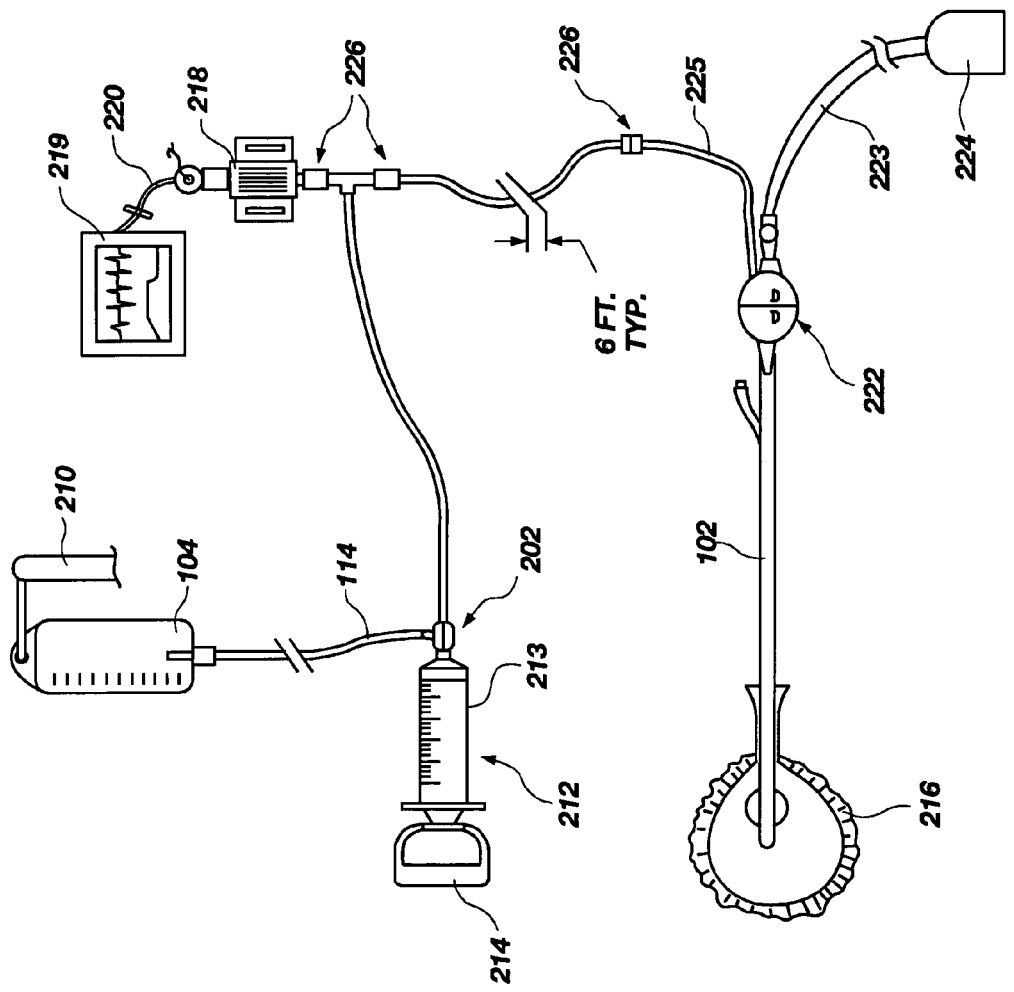
FIG. 3 illustrates a first currently preferred arrangement of equipment for measuring a patient's bladder pressure that locates a pressure transducer remote from the patient, and is depicted in urine drain mode.

FIG. 3 illustrates an arrangement of equipment for measuring intra-abdominal pressure in a patient that locates most of the equipment at a location remote from the patient. While equipment can be located at any convenient distance from the patient, it is generally located within a radius of about six to ten feet, or so. The intra-abdominal pressure measurement equipment desirably is assembled using a procedure operable to resist compromising sterility of the catheter draining system.

In the illustration of FIG. 3, apparatus including the saline fluid source 104 can be suspended from equipment stands, such as stand 210. Fluid flow control device 202 and syringe 212 may be located in convenient proximity to the saline bag 104. Illustrated syringe 212 is representative of a larger model, perhaps having a volume capacity of 50 cc. Such a syringe 212 typically is operated using both hands. An operator grasps the syringe barrel 213 with one hand and actuates the plunger held in the palm of the other hand at transverse handle 214. Cyclic actuation of the syringe 212 automatically operates the fluid flow control device 202 to urge fluid flow in the direction toward the patient's bladder 216.

Pressure transducer 218 desirably is suspended from some structure at an elevation in correspondence with the patient's bladder. Transducer 218 can be affixed to a wall, stand 210, a side of the patient's bed, or any other convenient location. Pressure display 219 can be placed for convenient monitoring by a health care practitioner. Electric cable 220 communicates the pressure signal from the transducer 218 to the display device 219.

The urine discharge valve illustrated in FIG. 3, and generally indicated at 222, is shown in a configuration for discharge of urine through urine catheter 102 placed into fluid communication with the patient's bladder 216. Valve 222 is normally placed into the position illustrated so that urine drains through valve 222, through drain conduit 223, and into urine bag 224. Some valves 222 may include one or more sections of conduit, such as drain conduit 223 and/or fluid supply conduit 225 permanently affixed to the body of the valve 222. In such case, a connector, such as the luer-locking type connector generally indicated at 226, may be provided to facilitate making plumbing connections in the intra-abdominal pressure monitoring apparatus assembly.

Figure 4:
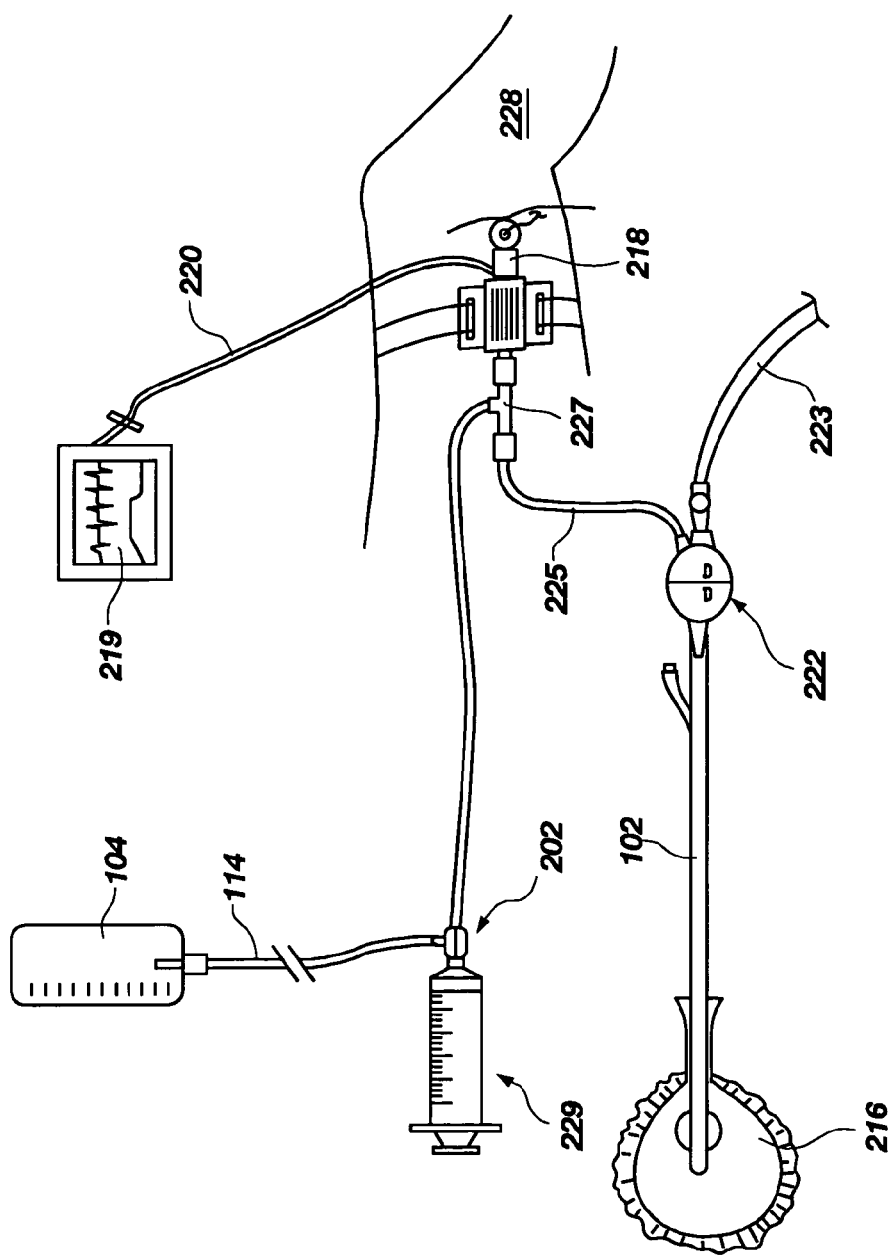
FIG. 4 illustrates a second currently preferred arrangement of equipment for measuring a patient's bladder pressure that locates a pressure transducer on the patient's leg, and is depicted in pressure measurement mode.

Referring now to FIG. 4, the arrangement to measure trends in intra-abdominal pressure locates the pressure transducer 218 on the patient's leg 228. A finger actuated syringe, generally indicated at 229, is illustrated in position for use as a fluid pump. The IAP valve, or urine valve 222 in FIG. 4, is illustrated as being oriented for fluid flow from fluid source 104 toward the patient's bladder 216 and for measurement of that fluid's pressure. The valve 222 may be characterized as a two-way valve in that fluid communication may be established through valve 222 between catheter 102 and either of fluid supply conduit 225 or drain conduit 223. That is, fluid communication can be established through only two of the three potential flow paths between three port openings. Valve 222 may also be characterized as providing a streamlined plumbing arrangement in that conduits 225 and 223 are maintained in approximately parallel alignment in the vicinity of the valve 222. In contrast to the orthogonal plumbing arrangement provided by certain prior art valves, such a streamlined plumbing configuration facilitates routing of the conduits to reduce irritation to a patient. The streamlined plumbing arrangement provided by valve 222 urges conduits 225 and 223 to follow a path between the patient's legs where the conduits are most out-of-the-way and less likely to impact negatively on patient comfort.

Figure 5:
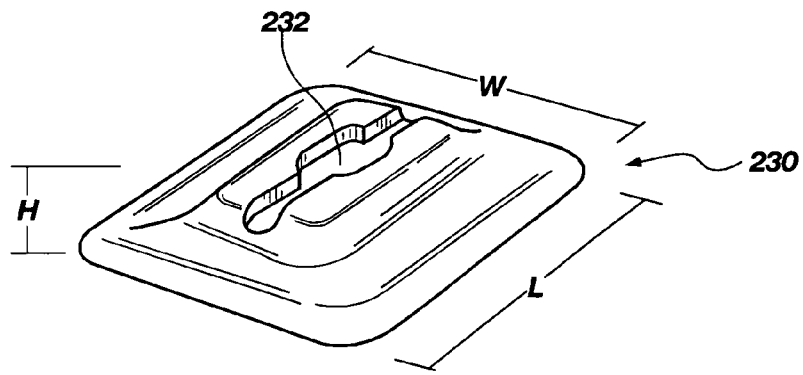
FIG. 5 is a top view in perspective of a protective housing embodied as a tray for disposition between a patient's legs.

FIG. 5 illustrates an optional housing or tray, generally indicated at 230, in which to hold portions of the assembly 200 and effective to resist patient irritation at a contact interface with the tray 230. Tray 230 effectively can shield the patient from contact with irritating portions of the assembly 200, including portions of the Foley catheter 102 and a urine discharge conduit occluding valve, if present. Tray 230 is placed in the patient's bed, typically between the patient's legs, and can shield the portion of the catheter 102 protruding from the patient.

Illustrated tray 230 can be described as having a width W, a length L, and a height H defining a volume that is somewhat pyramidal in shape. Tray 230 may be solid or hollow. A solid embodiment within contemplation can be made from a foam material. One hollow embodiment can be formed from a plastic shell. Desirably, edges and corners of tray 230 are blunted to provide a structure operable to reduce or minimize skin irritation on contact with the patient. Tray 230 may be manufactured from any material suitable for exposure to a patient's skin and operable in such a medical environment. The installed location for a tray 230 may be exposed to fecal material and other contaminants associated with a bedridden patient. Therefore, the tray 230 desirably is nonporous, or has a nonabsorbent skin, and has structure arranged to facilitate cleaning. Desirably, narrow crevices are avoided to facilitate cleaning of a fouled tray 230. Certain trays 230 may be formed, at least in part, from a material that can withstand a sterilization process to permit reuse.

The volume occupied by tray 230 provides a ramp-like surround, or shield, in which is formed a receiving socket 232. Socket 232 may be structured to receive the portion of the catheter 102 protruding from the patient and/or other structure, such as a valve 204. Tray 230 may also be adapted to orient conduits 106B and 120 for routing in substantially parallel configuration toward a patient's feet. Therefore, use of a tray 230 permits use of valves 204 having structure, such as protruding actuator levers and/or orthogonal conduit connection orientations, that would be uncomfortable to impress into a patient's skin. For example, certain trays 230 may include a socket 232 adapted to help guide fluid conduits attached to a "T" shaped two-way or three-way valve so that the conduits leave the socket 232 oriented substantially in parallel for routing those conduits in the space between a patient's legs.

Preferred trays 230 have a socket 232 adapted to hold structure(s) associated with the catheter to aid a health care practitioner during insertion of a needle into the aspiration port 125. Such a configuration for a socket 232 can be effective in reducing undesired needle sticks in both the patient and the health care practitioner.

Figure 6:
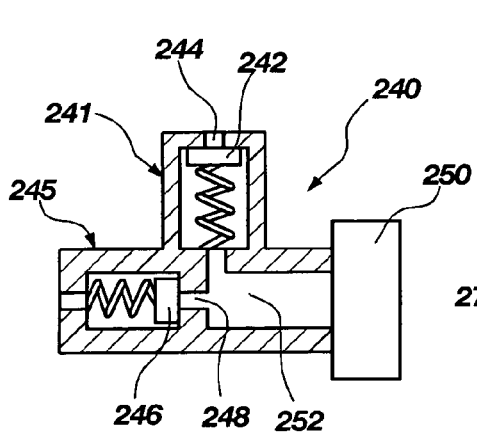
FIG. 6 is a side view, partially in section, illustrating a double check valve.
Figure 7:
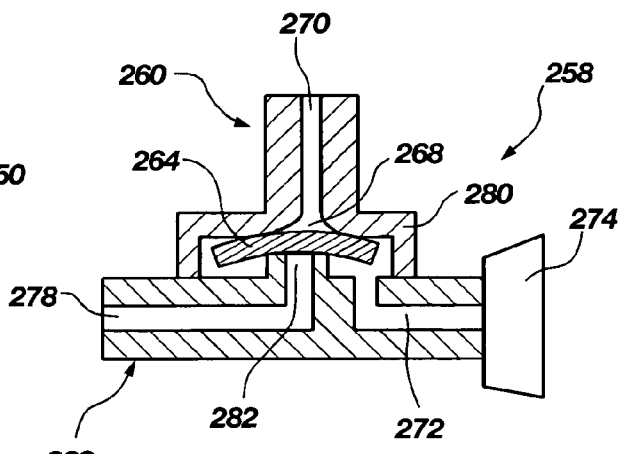
FIG. 7 is a side view, partially in section, illustrating a check-bypass valve operable as a double check valve in the invention.
Figure 8:
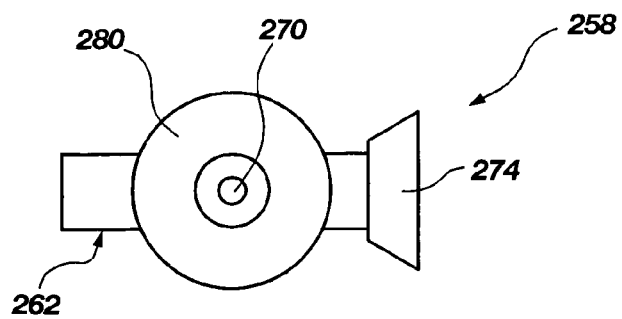
FIG. 8 is a top view of the valve of FIG. 7.
Figure 12:
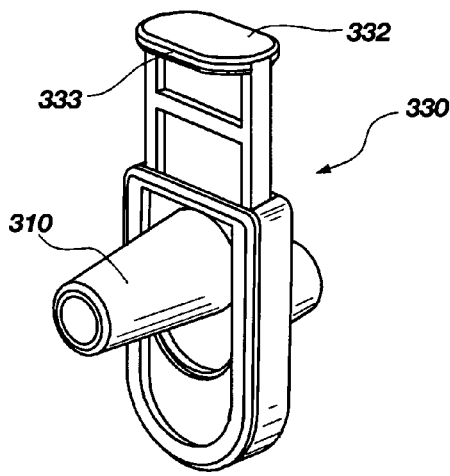
FIG. 12 is a view in perspective from a proximal end of a second urine valve.

FIGS. 6 through 8 illustrate two types of valves that are operable for use as an automatic flow-control device 202 (see FIG. 2). FIG. 6 illustrates a double check valve, generally indicated at 240. One check valve portion, generally indicated at 241, is formed by a sealing element 242 normally biased into engagement with an inlet opening or port 244. A second check valve portion, generally indicated at 245, is formed by sealing element 246 normally biased into engagement with exit port or opening 248. A pressure-cycling pump device, such as a syringe 116, may be connected in fluid communication with exit port 248 at a third port or conduit through connector 250. The syringe 116 cyclically effects the fluid pressure at a staging area 252 and thereby automatically operates the check valve portions 241 and 245 in correspondence with the high or low pressure generated by the syringe.

Of course, a fluid circuit equivalent to a fluid flow-control device, such as double check valve 240, can be formed by a pair of single check valves and a syringe 116 (or other cyclic-pressure pump) disposed between the two individual check valves. In certain embodiments, a single check valve may be included in a pressure measuring apparatus 200. In one such embodiment, the discrete check valve is located in the fluid path between a fluid source and a syringe 116 to enable multiple syringe discharges without requiring manual valve adjustments to reload the syringe with fluid.

FIGS. 7 and 8 illustrate an embodiment of a check-bypass valve, generally indicated at 258, configured for use in the instant invention. Valve 258 includes a check valve portion, generally indicated at 260, and a bypass valve portion, generally indicated at 262. Check valve portion 260 is formed by resilient member 264 biased into normally sealed engagement over orifice 268. In operation of check valve 260, fluid flows into supply port 270, and past resilient member 264, to a staging area 272. In accordance with one definition of a check valve, fluid flow in the reverse direction would cause seal member 264 to seal tighter over orifice 268, thereby further resisting the flow.

Typically, staging area 272 is in fluid communication with a syringe, such as syringe 116 illustrated in FIG. 2. A cyclic pump may alternatively be employed to vary the pressure in the staging area 272 to operate the valve 258. A syringe 116 may be attached directly to connection structure 274 or may be spaced apart from the valve 258 by use of structure(s) such as a length of tubing.

It is currently preferred for connection structure 274 to be structured as a LUER-LOK™ type fitting and for structure surrounding inlet port 270 and discharge port 278 to accommodate attachment of tubing by way of a press-on fit. However, connection structure 274 may be structured as any other operable connecting structure, including barbs configured for press-fit reception in, or over, a conduit. Likewise, any portion of a valve 258 (or a valve 240), that is adapted for connection to a fluid conduit or other device may be structured to form a press-together fit, or to incorporate a portion of a LUER-LOK™ type joint, or a threaded connection, or as any joint providing fluid through-flow and structured to resist fluid leaks.

The illustrated bypass valve portion 262 can operate substantially as a check valve. However, under certain conditions, fluid can flow in either direction between port 278 and staging area 272. In use with the instant invention, pressurized fluid in the staging area 272 causes resilient seal member 264 to deflect into the orifice 268 of housing 280, thereby opening a flow path from staging area 272 though exit port 282 and out of discharge port 278. Contrary to a true check valve, increased fluid pressure at exit port 282 tends to open the flow path by lifting seal member 264 from engagement over exit port 282. Therefore, in certain situations, fluid could flow from discharge port 278 and into staging area 272. In that event, the fluid presumably could be refilling a syringe.

Bypass valve 262 is normally closed. Resilient member 264 is biased into sealing engagement over exit port 282 during assembly of the valve 258. Therefore, valve 262 operates as a check valve to permit fluid flow in only one direction until fluid pressure at exit port 282 builds to a value operable to overcome the bias in member 264. For low pressure applications, such as in measuring abdominal pressure, bypass valve portion 262 acts as a check valve.

With continued reference to FIG. 2, certain preferred embodiments of a urine control valve 204 may include a valve body or housing 290 shaped to provide a comfortable interface for adjacent surfaces of a patient's skin to resist contact-induced patient discomfort. One such comfort-enhancing shape includes blunt edges and rounded corners. Valve actuation structure for a comfort-designed urine valve 204 desirably is structured to avoid protruding elements that might irritate a patient.

FIGS. 9 through 11 illustrate certain details of construction of a first urine valve, generally indicated at 300, that is configured to provide a streamlined plumbing arrangement to enhance routing of conduits between a patient's legs. Valve 300 includes a valve body 302, a shuttle or valve gate 304, and a cap 306. A proximal conduit stub forming urine port 310 is placed through window 312 in cap 306 as the valve 300 is assembled. Cap 306 is typically bonded or ultrasonically welded to valve body 302, trapping gate 304 sandwiched between the cap 306 and valve body 302. Gate 304 can slide between in board and outboard positions defined by a structural interference between urine port 310 and window 312.

Valve 300 is configured to provide two alternative, and preferably mutually exclusive, fluid flow paths through the valve. When urine port 310 is placed, as illustrated in FIGS. 9 and 10, at an inboard position in window 312, lumen 314 passing through urine port 310 is placed into alignment for fluid communication with urine discharge port 316. Grip structure 318 is provided to assist in moving gate 304 to an outboard position. At the outboard position, bore 314 is placed into alignment for fluid communication through fluid supply port 320.

FIGS. 12 through 15 illustrate a second embodiment of a valve, generally indicated at 330, that is configured to provide a streamlined plumbing arrangement to enhance routing of conduits between a patient's legs. Valves 300 and 330 are both of the type that maybe characterized as transversely actuated gate valves, with a principal difference being the arrangement of gripping structure to actuate the valve gate 304. Valve 330 has gripping structure 332 arranged to provide a transversely oriented shelf 333. FIGS. 12 through 15 illustrate valve 330 oriented with gate 304 located at an outboard position to align urine port 310 for fluid communication with fluid supply port 320.

Figure 13:
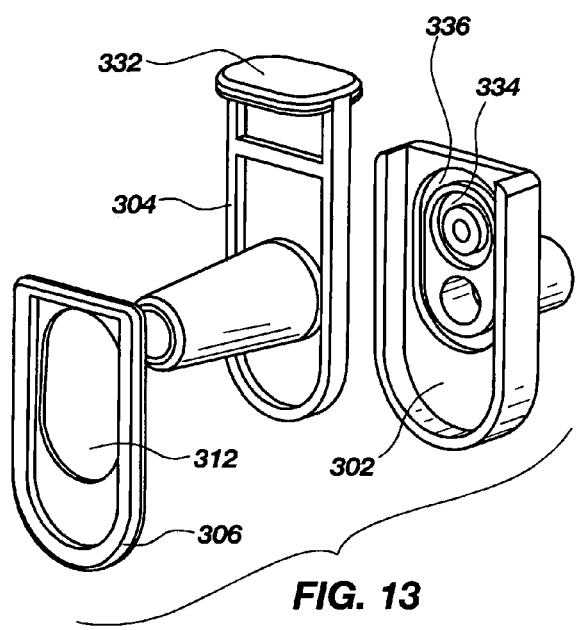
FIG. 13 is an exploded view in perspective of the urine valve illustrated in FIG. 12.
Figure 14:
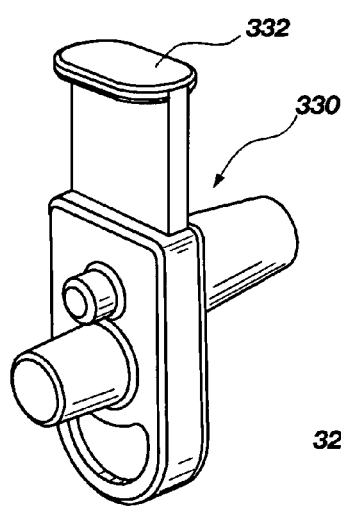
FIG. 14 is a view in perspective from a distal end of the second urine valve.
Figure 15:
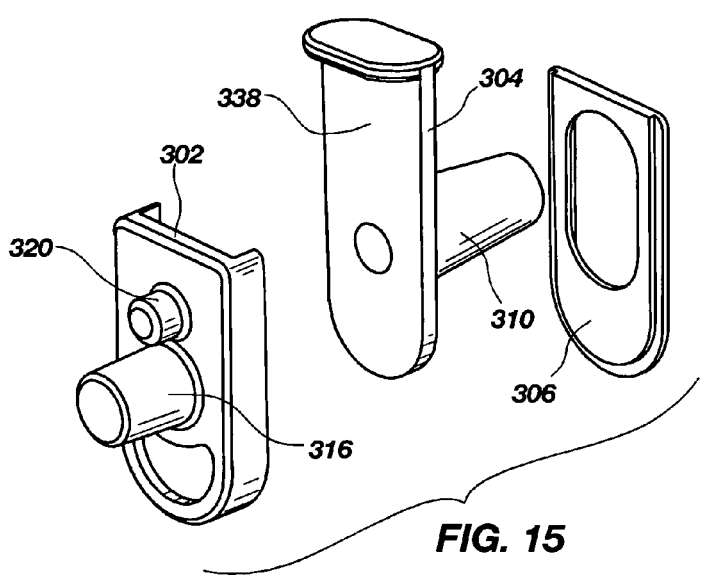
FIG. 15 is an exploded view in perspective of the urine valve illustrated in FIG. 14.
Figure 22:
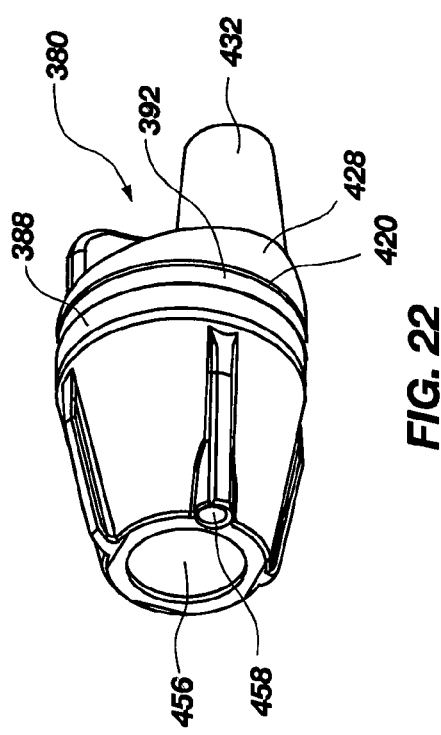
FIG. 22 is a view in perspective from a distal end of the fourth urine valve, but with the hose barb removed.

FIG. 13 illustrates one arrangement operable to resist fluid leaks from the fluid flow paths through the valve 330. Grooves 334 and 336 receive O-rings that are adapted to bear against surface 338 of gate 304 (see FIG. 15). It is alternatively within contemplation to form a raised lip about respective openings of lumens through fluid supply port 320 and urine drain 316. Such raised lips may replace the O-ring seals (not illustrated), and bear against surface 338 to form fluid-tight seal structure. In such case, and to enhance sealing, material forming gate 304 desirably would be softer than material forming a valve body 302. In any case, it is desirable to form valve seals in a single plane to minimize the amount of fluid trapped in a "dead" space between seal elements to resist chance of transfer of contamination or disease.

It is desirable to minimize back-wash of trapped fluid when pumping fluid into a patient's bladder to make an intra-abdominal pressure measurement. Single-sided gate valves, such as valves 300 and 330, advantageously confine a minimal "dead" volume when actuated between flow path configurations. "Dead" volume is defined as the volume trapped within a valve body by seal structure, such as by an O-ring contained in groove 336 and operable as a secondary or intermediate seal. A dead volume may provide a habitat in which disease or microorganisms may grow.

For purpose of dead volume calculation, one side of a "volume" (e.g. at an end of a fluid supply conduit) may sometimes be regarded as being bounded by a plane offset from a seal surface (e.g. surface 338) and passing through an edge of a sealing O-ring. Such a volume can essentially be considered as being contained within a perimeter formed by a compressed O-ring. In one embodiment of a valve having a seal structure constructed as depicted by valves 300 and 330, the dead volume has been calculated as being about 0.0006 cubic inch. In contrast, if that valve arrangement were formed to have a two-sided gate seal, the corresponding dead volume (including the passageway through the gate) would be about 0.0036 cubic inch.

Fluid carrying conduits can be attached to urine valves, such as valves 300 and 330, when constructing a pressure measuring assembly for use on a patient, or may be affixed to one or more valve ports during a valve assembly procedure. For example, it is currently preferred to include a short length, or pigtail, of fluid supply conduit affixed to fluid supply port 320. Fluid supply conduits typically are of relatively small diameter (e.g. about 1/16 to 1/8 inch in inside diameter) to minimize priming volume. Such a conduit typically is solvent welded or otherwise bonded to port 320. The urine drain lumen downstream of the catheter and passing through the urine valve desirably is of relatively larger diameter (e.g. about 3/16 to 1/2 inch in inside diameter) to resist occlusion during extended periods of use. A discharge end of a catheter 102, or tube section 106A (see FIG. 2), may be stretch-fit over an exterior surface of urine port 310. In some cases, an additional external clamp may further be applied over the catheter 102 or conduit 106A to augment the formed joint and to resist decoupling the conduit from the port 310 as a bolus of fluid is introduced into a patient's bladder. Similarly, a discharge conduit 106B may be attached to urine drain 316 in a plug-together fit.

FIGS. 16 through 19 illustrate a third embodiment of a valve, generally indicated at 350, that is configured to provide a streamlined plumbing arrangement to enhance routing of conduits between a patient's legs. Valve 350 is of the type that may be characterized as a rotary actuated gate valve. Valve 350 includes a valve body 352, a rotary gate 354, and a valve cover 356. Body 352 carries grooves 358 and 360 that may hold O-rings or may provide clearance to promote sealing of lips 362 and 364 against gate surface 366.

A change in selected flow paths through the illustrated valve 350 is effected by an approximately 90 degree rotation of gate 354 relative to valve body 352. A lever 368 is trapped within arcuate slot 370 during assembly of the valve 350 and is operable to rotate gate 354 to a desired position to permit fluid communication between urine conduit 372 and either of fluid supply port 374 or urine drain 376. Assembly of valve 350 typically is accomplished by ultrasonically welding cover 356 to valve body 352. An alternative bonding process may also be used, perhaps incorporating a UV-activated or other adhesive or solvent welding.

As illustrated in FIGS. 17 and 19, a fluid seal typically is formed on each of the surfaces forming opposite sides of gate 354. However, gate 354 may be made thin to minimize, or at least reduce, dead volume (trapped in a port through the gate thickness and between sealing planes) to reduce potential for culturing or transmission of disease. A redundant, or back-up, fluid seal generally is formed by an O-ring carried in groove 377. Such a seal is redundant to the fluid seals formed by O-rings carried in grooves 358 and 360 and also resists penetration of contaminants into the interior of the valve 350. Similarly, an O-ring carried in groove 378 desirably forms a seal on an opposite surface of gate 354 to resist both leaking and contamination of the interior of valve 350.

FIGS. 20 through 27 illustrate fourth and fifth valve embodiments, generally indicated at 380 and 385 respectively, that are configured to provide a streamlined plumbing arrangement to enhance routing of fluid conduits between a patient's legs. Valves 380 and 385 are also of the type that may be characterized as a rotary actuated gate valve. Valves 380 and 385 each include a valve body 388, a rotary gate 390, and a capture ring 392. Body 388 preferably carries grooves 394 and 398 in which to receive O-rings 400 and 402, respectively. Again, valve seals provided by O-rings 400 and 402 may alternatively be structured as lips or protrusions carried by body 388 and arranged to press against gate surface 404 to form a fluid resistant seal. The principal difference between valves 380 and 385 is the conformation of their distal housings, 408 and 410, respectively.

Assembly and operation of valve 380 will now be described with particular reference to FIGS. 21 and 23. O-rings 400 and 402 are placed into grooves 394 and 398, respectively. Then a rotary gate 390 is placed onto the exposed portions of the O-rings. Gate 390 is oriented to locate detent 414 in the space provided by arcuate slot 416. Gate 390 can therefore rotate between limits formed by a structural interference formed between detent 414 and opposite ends of arcuate slot 416. Valve body 388 is then joined to retainer ring 392 to capture and permit rotation of the gate 390. Distal ring 417 rides on circumferential bearing surface 418 to hold gate 390 in sealing axial engagement with O-rings 400 and 402. A notch in capture ring 392, generally indicated at 419, provides clearance for detent 414. It is also within contemplation to form detent 414 with a step shape to accommodate a ring 417 that has an uninterrupted circumference.

Infiltration of external contamination to the inside of a valve 380 is resisted by O-ring 420. O-ring 420 is received on shoulder 422 carried on a proximal end of capture ring 392. A distal end 426 of proximal housing 428 is adapted to ride on O-ring 420 and to compress the O-ring 420 against shoulder structure 422 to seal the valve 380. It is currently preferred to form a valve, such as valve 380, to facilitate cleaning the exterior surface of the valve 380. Therefore, it is desirable to avoid crevices where contaminants may remain subsequent to wiping the exterior surface of the valve 380. The seal formed by O-ring 420 is adapted to facilitate cleaning of a patient's bodily excretions or other contaminants from an exterior of the valve 380.

In general, proximal housing 428 can be held in an assembled axial position in a valve 380 by forming a joint between structure carried by the housing 428 and structure carried by the gate 390. As illustrated, extension conduit 430 (FIG. 23) from urine port 432 is affixed to socket 434 (FIG. 21) carried on gate 390. Similarly, a distal end of post 440 is attached to socket 442. Gate 390 is held by post 440 and conduit 430 and rotates with housing 428.

Figure 23:
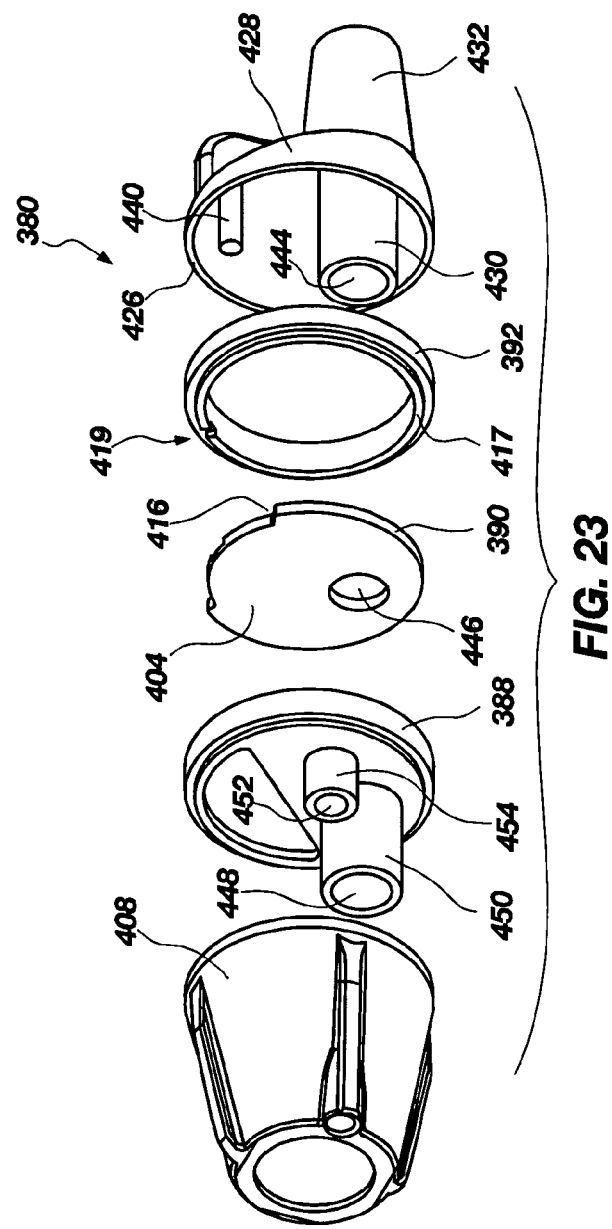
FIG. 23 is an exploded view in perspective of the urine valve illustrated in FIG. 22.

With reference to FIG. 23, a flow path through the urine valve 380 includes lumen 444 extending through urine port 432 and extension conduit 430. Lumen 444 is fixed in fluid communication with aperture 446 passing through gate 390 during assembly of valve 380. The remainder of a flow path through valve 380 is dependent upon the rotational orientation of gate 390. At one gate orientation, aperture 446 is placed into fluid communication with lumen 448 extending through urine discharge port 450. Such an orientation for valve gate 390 is the typical valve configuration and permits continual draining of urine from an installed urinary catheter. At another gate orientation, aperture 446 is placed into fluid communication with lumen 452 extending through fluid supply port 454. Therefore, fluid communication through two-way urine valve 380 can be provided either through lumen 448 or lumen 452. The latter gate orientation permits a fluid bolus to be injected into the patient's bladder for intra-abdominal pressure measurement.

Proximal housing 428 and distal housing 408 provide a torpedo-shape to the urine valve 380. A torpedo-shape enhances patient comfort by reducing or minimizing protruding portions from a valve that might irritate the patient's skin when contacted. Preferred torpedo-shapes generally are defined by valve structure that is somewhat elongate and cylindrical. Advantageously, such valve structure also tapers to a reduced size at proximal and distal ends. A torpedo-shaped valve can also operate to streamline fluid conduit plumbing in the vicinity of the valve. Such structure can be contrasted to commercially available two-way valves that generally orient one conduit connection at a right angle to a pair of typically in-line conduit connections, forming a "T" shape.

It is currently preferred to include sections of tubing, such as tubing 223 and 225 depicted in FIG. 3, affixed to a valve, such as valve 380. When present, a conduit 225 can be solvent welded inside lumen 452. A conduit section corresponding to at least a portion of urine drain 223 illustrated in FIG. 3, can be similarly installed inside lumen 448, or may be stretched in a plug fit over port 450. Of course, such portions of fluid conduits would first be threaded through apertures 456 and 458 (see FIG. 22) in distal housing 408. Subsequent to affixing such conduit portions in place on valve body 388, distal housing 408 can be attached to valve body 388.

Desirably, apertures 456 and 458 are sized in close conformance to a diameter of conduit sections passing therethrough. Close agreement in size between the aperture and the conduit it surrounds facilitates maintaining the valve 380 in a clean state. It is within contemplation also to provide a plug or stopper to occlude any open portions of an aperture between a conduit and an aperture wall. Valve 385, illustrated in FIGS. 24 through 27, has a distal housing specifically shaped to form apertures 460 and 462 that are in such close agreement with a respective fluid supply conduit and a urine drain conduit.

Certain valves, such as torpedo valves 380 and 385, benefit from the presence of indicia to show the current flow path through the valve. In valve 380 (see FIG. 21), an indicator flap 466 is placed into axial agreement with either alignment indicator 468 or 470 to place valve 380 into drain mode or intra-abdominal pressure mode, respectively. Indicators 466, 468, and 470 are illustrated as protruding slightly from a surface of housings 428 and 408 to provide tactile and visual feedback to a valve operator. Alignment flaps 472 and 474 carried on proximal and distal housings of valve 385 are placed into axial agreement to place valve 385 into a urine drain configuration. Such indicators 472 and 474 provide visual feedback to remind a health care practitioner to return a valve 385 to a urine drain mode.

It is currently preferred for a urine valve to maintain a "smooth" contact area, at a potential patient interface, when rotated to either pressure measurement or urine draining positions. Also, the indicator structures 466–474 desirably have a relatively low profile to avoid inflicting patient discomfort if brought into contact with the patient's body. It is also within contemplation to apply areas of different color to portions of the respective housings to alternatively, or additionally, indicate a valve flow path setting. It is further within contemplation to provide written indicia to spell out a flow path corresponding to a particular valve orientation.

It is currently preferred to injection mold valve components in straight-pull, simple molds to reduce mold-making and attendant manufacturing costs. Valves may be formed from a variety of medical grade plastics, including polycarbonate, ABS, acrylic, and polyethylene. O-ring seals may be formed from suitable rubber-like materials, with silicone currently being preferred. A variety of bonding procedures are operable to join valve components to form a valve assembly, including plastic welding techniques such as solvent, ultrasonic, friction, shear, and heat welding, as well as adhesive bonding techniques.

With reference again to FIGS. 20 and 21, sometime a hose barb, generally indicated at 478, desirably is included on a urine port 432 to resist decoupling of a urinary catheter 102 connected to the port 432. One way to include such barb structure 478 in a straight-pull molded part is as the illustrated add-on ring 480. Ring 480 typically is affixed to port 432 with an adhesive procedure, although welding or other attachment constructions are also effective. As an additional safeguard to resist decoupling of a urinary catheter 102, a clamp 484 may additionally be provided for installation on top of catheter 102 once the catheter 102 is installed in a press-fit over the barb structure 478. A clamp 484 desirably is both self-biased and structured to avoid protrusions that might injure or bother a patient on contact.

What is claimed is:

1. An apparatus for measuring hydraulic pressure in the bladder of a medical patient whereby to infer intra-abdominal pressure, comprising:
    a catheter adapted for draining urine from said medical patient;
    a container of fluid;
    a first fluid path comprising conduit disposed between said container and a drain portion of said catheter;
    a fluid pump disposed to urge fluid to flow through said first fluid path;
    a pressure transducer arranged to measure a pressure of fluid in said first fluid path; and
    an automatic flow-control device actuated, by fluid pressure effected by said fluid pump, said automatic flow-control device being disposed in said first fluid path and comprising a valve element having a first surface and a second surface, and with said valve element being arranged such that the first surface may be displaced by suction action of said fluid pump to permit flow of fluid from said container toward said fluid pump while the second surface resists flow of fluid from said catheter toward said fluid pump, and the second surface may be displaced by expulsion action of said fluid pump to permit flow of fluid from said fluid pump toward said catheter while the first surface resists flow of fluid toward said container.

2. The apparatus of claim 1, wherein:
    said automatic flow-control device comprises a check-bypass valve; and
    said fluid pump is configured to effect a cyclic fluid pressure at a staging area between a check valve seal and a bypass valve seal.

3. The apparatus of claim 2, wherein:
    said fluid pump comprises a syringe; and
    said check-bypass valve is adapted for attachment to a discharge end of said syringe.

4. The apparatus of claim 1, further comprising:
    a urine valve configured to provide:
        a first flow portion of said urine valve disposed in said first fluid path;
        a second flow portion of said urine valve disposed in a second fluid path operable as a drain for fluid discharged from said catheter; and
        a third flow portion of said urine valve disposed for fluid communication with a urine discharge end of said catheter; wherein:
    said urine valve is operable selectively to resist fluid flow between said third flow portion and said second flow portion.

5. The apparatus of claim 4, wherein:
    said urine valve is operable selectively to resist fluid flow between said first flow portion and said third flow portion.

6. The apparatus of claim 4, wherein:
    said first flow portion and said second flow portion of said urine valve provide a structure configured to permit connection to respective first and second substantially parallel conduit end portions to facilitate routing substantially parallel conduits in a space between the legs of said medical patient.

7. The apparatus of claim 4, wherein:
    said first flow portion, said second flow portion, and said third flow portion of said urine valve comprise substantially parallel conduit sections.

8. The apparatus of claim 4, wherein:
    a connection structure is provided in fluid communication with each of said first flow portion, said second flow portion, and said third flow portion of said urine valve for connection of first, second, and third substantially parallel conduit end portions thereto to facilitate routing substantially parallel conduits in a space between the legs of said medical patient.

9. The apparatus of claim 4, wherein:
    a body of said urine valve comprises a housing defining an envelope arranged for contact with said medical patient and structured to resist imparting contact injury from structure associated with said urine valve to said medical patient.

10. The apparatus of claim 9, wherein:
    a flow path through said urine valve is selected by rotating a first valve structure with respect to a second valve structure.

11. The apparatus of claim 10, said urine valve being actuated to select a fluid flow path by rotating a first portion of said housing with respect to a second portion of said housing.

12. The apparatus of claim 11, wherein:
    said first portion and said second portion of said housing are sealed against infiltration by external contaminants.

13. The apparatus of claim 9, wherein:
    said housing comprises smooth surfaces and rounded corners to resist formation of crevices in which contaminants might be shielded, whereby to facilitate cleaning fecal matter from an exterior surface of said housing.

14. The apparatus of claim 4, wherein:
    said urine valve is structured as a gate valve.

15. The apparatus of claim 4, wherein:
    a first aperture and a second aperture, each opening to portions of respective first and second flow paths through said urine valve, are disposed on a first surface; and
    a valve core element comprises a second surface structured in cooperation with said first surface such that a third aperture disposed on said second surface can be aligned to form a leak resistant seal for fluid communication with either of said first and second apertures, said third aperture opening to a portion of a flow path in common to said first and said second flow paths.

16. The apparatus of claim 15, wherein said leak resistant seal comprises:
a first O-ring disposed on said first surface and arranged to encompass said first aperture; and
a second O-ring disposed on said first surface and arranged to encompass said first aperture and said second aperture.

17. The apparatus of claim 4, further comprising:
a structure carried on a housing of said urine valve adapted to provide visual indication of a currently selected flow path.

18. The apparatus of claim 4, in combination with:
a tray adapted for disposition on a bed and operable as a protective housing, said tray having blunt corners and areas of gradual transition in curvature whereby to resist injury to said medical patient arising from contact therewith, said protective housing defining a socket operable to space a structure received in said socket apart from said medical patient, said socket being structured to receive said urine valve.

19. The combination of claim 18, wherein:
said socket is configured to accommodate a discharge end portion of a structure associated with said catheter.

20. The combination of claim 19, wherein:
said socket is adapted to hold said discharge end portion in a preferred orientation whereby to assist a health care practitioner in inserting a needle into an aspiration port associated with said catheter.

21. An apparatus for measuring hydraulic pressure in the bladder of a medical patient, comprising:
a catheter adapted for draining urine from said medical patient;
a container of fluid;
a first fluid path between said container and a drain portion of said catheter;
a fluid pump disposed in said first fluid path;
a pressure transducer configured to measure a pressure of fluid in said first fluid path at a location downstream of said pump; and
a multi-way valve comprising:
a first flow portion along a first axis disposed in said first fluid path and arranged to receive fluid from said container;
a second flow portion along a second axis disposed in a second fluid path configured as a drain for said catheter; and
a third flow portion along a third axis disposed in said first fluid path for fluid communication with a urine discharge end of said catheter; wherein:
said first axis, said second axis, and said third axis are disposed substantially in parallel; and
said multi-way valve is operable selectively to resist fluid flow between said third flow portion and said second flow portion.

22. The apparatus of claim 21, said multi-way valve providing a respective connection structure in fluid communication with each of said first, second and third flow portion that is configured for connection to a cooperating one of a plurality of substantially parallel end portions of fluid conduits to provide a streamlined plumbing arrangement to facilitate parallel routing of said fluid conduits between the legs of said medical patient.

23. The apparatus of claim 22, wherein:
a urine draining lumen forming a flow path through said multi-way valve has a diameter in excess of about 3/16 inches; and
a sealing element of said multi-way valve is structured to contain a dead volume of less than about 0.0006 cubic inches to reduce contaminant containment, whereby to resist infection transmission.

24. A method for measuring hydrostatic pressure in the bladder of a medical patient, comprising:
a) installing a urinary catheter in said medical patient to provide fluid communication in a first fluid path comprising a stretch between said bladder and a discharge portion of said catheter;
b) disposing an inlet port of a urine valve in fluid communication with said first fluid path, said urine valve comprising a drain orientation and a measure orientation, said drain orientation providing communication between said inlet port and a second fluid path directed from said urine valve toward a drain receptacle, said measure orientation providing communication between said inlet port and a third fluid path between said urine valve and a source of fluid, said urine valve comprising a housing defining an envelope arranged for contact with said medical patient and structured to resist imparting contact injury from structure associated with said urine valve to said medical patient;
c) connecting said source of fluid to a pump operable to urge a fluid along said third fluid path toward said catheter;
d) disposing a pressure transducer to measure pressure of fluid between said pump and said bladder;
e) placing said urine valve into said measure orientation and operating said pump to introduce a bolus of said fluid into said bladder;
f) using said pressure transducer to measure a hydrostatic pressure of said fluid; and
g) placing said urine valve into said drain orientation.

25. The method according to claim 24, wherein steps e) through g) are repeated in sequence as an intra-abdominal pressure measurement procedure is performed a plurality of instances that are spaced apart in time.

26. The method of claim 24, wherein operation of said pump in step e) comprises actuation of a syringe to cause cyclic pressure fluctuation at a staging area of an automatic valve arrangement operable to permit fluid flow from said fluid source toward said catheter and to resist fluid flow in a reverse direction.

* * * * *

UNITED STATES PATENT AND TRADEMARK OFFICE
CERTIFICATE OF CORRECTION

PATENT NO. : 7,112,177 B2
APPLICATION NO. : 10/379222
DATED : September 26, 2006
INVENTOR(S) : Mark A. Christensen et al.

Page 1 of 1

It is certified that error appears in the above-identified patent and that said Letters Patent is hereby corrected as shown below:

On the title page:
In ITEM (56), "References Cited,"
  OTHER PUBLICATIONS

| | |
|---|---|
| Page 1, 2nd column, 3rd line, | change "Journal og" to --Journal of-- and change "Criitical Care" to --Critical Care-- |
| Page 2, 1st column, 4th line, | change "Lozen, Yvonne" to --Lozen, Yvonne,-- |
| Page 2, 2nd column, 11th line, | change "PCT Writtern Opinion" to --PCT Written Opinion-- |

In the specification:

| | | |
|---|---|---|
| COLUMN 1, | LINE 32, | change "intra abdominal intra-abdominal" to --intra-abdominal-- |
| COLUMN 2, | LINE 8, | change "stopcock 10" to --stopcock 110-- |
| COLUMN 2, | LINE 10, | change "syringe 16" to --syringe 116-- |

Signed and Sealed this

Eighteenth Day of March, 2008

JON W. DUDAS
*Director of the United States Patent and Trademark Office*